(12) United States Patent
Ford et al.

(10) Patent No.: US 9,079,925 B2
(45) Date of Patent: Jul. 14, 2015

(54) ALKALINE EARTH METAL-COMPLEXED METAL AMIDES

(71) Applicants: BAYER INTELLECTUAL PROPERTY GMBH, Monheim (JP); BAYER CROPSCIENCE AG, Monheim (DE)

(72) Inventors: Mark James Ford, Schmitten (DE); Marc Mosrin, Frankfurt (DE)

(73) Assignees: BAYER INTELLECTUAL PROPERTY GMBH, Monheim (DE); BAYER CROPSCIENCE AG, Monheim (DE)

( * ) Notice: Subject to any disclaimer, the term of this patent is extended or adjusted under 35 U.S.C. 154(b) by 0 days.

(21) Appl. No.: 14/378,537

(22) PCT Filed: Feb. 13, 2013

(86) PCT No.: PCT/EP2013/052833
§ 371 (c)(1),
(2) Date: Aug. 13, 2014

(87) PCT Pub. No.: WO2013/120878
PCT Pub. Date: Aug. 22, 2013

(65) Prior Publication Data
US 2015/0031886 A1 Jan. 29, 2015

(30) Foreign Application Priority Data

Feb. 17, 2012 (EP) .................................. 12155977
Feb. 17, 2012 (EP) .................................. 12155980
Jun. 13, 2012 (EP) .................................. 12171860
Jun. 13, 2012 (EP) .................................. 12171862

(51) Int. Cl.
C07F 3/06 (2006.01)
C07F 3/04 (2006.01)
C07F 3/02 (2006.01)
C07D 211/12 (2006.01)

(52) U.S. Cl.
CPC ................ *C07F 3/06* (2013.01); *C07D 211/12* (2013.01)

(58) Field of Classification Search
CPC ..................................... C07F 3/06; C07F 3/02
USPC ............................................................. 546/11
See application file for complete search history.

(56) References Cited

U.S. PATENT DOCUMENTS 8,513,416 B2 * 8/2013 Knochel et al. ................. 546/11

FOREIGN PATENT DOCUMENTS

WO      2008138946 A1    11/2008
WO      2010092096 A1     8/2010
WO   WO 2010092096 A1 *  8/2010

OTHER PUBLICATIONS

International Search Report received in corresponding PCT/EP2013/052833, mailed Apr. 22, 2013.
Mosrin, et al., "TMPZnCl-LiCl: A New Active Selective Base for the Directed Zincation of Sensitive Aromatics and Heteroaramatics", Organic Letters, 2009, vol. 11, No. 8, 1837-1840.

* cited by examiner

*Primary Examiner* — Yong Chu
(74) *Attorney, Agent, or Firm* — Miles & Stockbridge P.C.

(57) ABSTRACT

The present invention relates to metal amides of the formula (I), to a process for preparation thereof and to the use thereof as bases for aromatics, heteroaromatics, alkenes, alkynes and other organic compounds having activated C—H bonds.

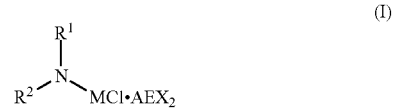

(I)

15 Claims, No Drawings

ALKALINE EARTH METAL-COMPLEXED METAL AMIDES

CROSS REFERENCE TO RELATED APPLICATIONS

This application is a §371 National Stage Application of PCT/EP2013/052833, filed Feb. 13, 2013, which claims priority to EP 12155980.1, filed Feb. 17, 2012, EP 12155977.7, filed Feb. 17, 2012, EP 12171860.5, filed Jun. 13, 2012 and EP 12171862.1, filed Jun. 13, 2012.

BACKGROUND

1. Field of the Invention

The present invention relates to metal amides of the formula (I), to a process for preparation thereof and to the use thereof as bases for metallation of aromatics, heteroaromatics, alkenes, alkynes and other organic compounds having activated C—H bonds.

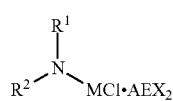
(I)

2. Description of Related Art

The preparation of aromatic and heteroaromatic molecules is of great significance because of the high biological potency thereof. Consequently, these structural elements are constituents of many active pharmaceutical and agrochemical ingredients. The direct metallation of aromatics, and also of activated C—H bonds, has become established as an excellent tool for functionalization of aromatics, heteroaromatics and other organic compounds.

For this purpose, predominantly lithium alkyls or lithium amides have been used to date as bases.

As an alternative, efficient bases have been developed for magnesiation and zincation of aromatics and heteroaromatics. Zinc amide or magnesium amide bases, for example Mg-TMP and Zn-TMP (TMP=2,2,6,6-tetramethylpiperidyl), complexed with lithium chloride, for example TMPMgCl·LiCl, TMPZnCl·LiCl, TMP$_2$Zn·2MgCl$_2$·2LiCl, are versatile metallation reagents, as has been described in WO 2010/092096 or WO 2008/138946. They have high kinetic basicity coupled with very good chemo- and regioselectivities. In addition, zinc amide bases can be stored under protective gas as solutions in THF for weeks, without losing their activity.

For synthesis of the bases, typically amines, for example TMP, are lithiated with equimolar amounts of butyllithium. Owing to the high cost of butyllithium, zinc amide bases are too expensive for a multitude of industrial syntheses. There is therefore an urgent need for a more favourable route to metal amide bases, especially dispensing with the use of expensive butyllithium.

The problem addressed by the invention was therefore that of overcoming the disadvantages described above.

SUMMARY

The object was achieved in accordance with the invention by a process for preparing metal amides of the formula (I)

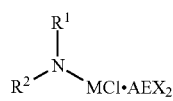
(I)

where
AE is an alkaline earth metal selected from calcium and magnesium;
M is a metal selected from metals from groups 3, 4, 7, 8, 9, 10, 11, 12, 13 of the Periodic Table of the Elements (PTE) and the group of the lanthanoids;
X is a halogen atom selected from the group consisting of fluorine, chlorine, bromine and iodine;
$R^1$ and $R^2$ are each independently selected from the group consisting of ($C_1$-$C_8$)alkyl optionally substituted by 1-2 $R^3$ radicals;
or
$R^1$ and $R^2$ together form a —(CH$_2$)$_4$—, —(CH$_2$)$_5$— or —(CH$_2$)$_2$O(CH$_2$)$_2$— group, where each of these groups may optionally be substituted by 1-4 $R^4$ radicals;
$R^3$ is independently selected from halogen, ($C_1$-$C_3$)alkoxy, ($C_1$-$C_3$)haloalkoxy and ($C_2$-$C_4$)dialkylamino;
$R^4$ is selected from halogen, ($C_1$-$C_3$)alkyl, ($C_1$-$C_3$)alkoxy, ($C_1$-$C_3$)haloalkoxy and ($C_2$-$C_4$)dialkylamino,
by reaction of chloroamines of the formula (II)

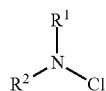
(II)

in which the $R^1$ and $R^2$ radicals are each as defined above with one or more metallic (i.e. present in elemental form) alkaline earth metals (AE) and/or one or more metals (M) (i.e. in elemental form), where AE and M are each as defined above.

As a result of the oxidative insertion of the metal (M) and/or alkaline earth metal (AE), the process according to the invention does not need butyllithium.

DETAILED DESCRIPTION OF A PREFERRED EMBODIMENT

In a preferred process according to the invention for preparation of AE-complexed metal amides of the above-defined formula (I), chloroamines of the above-defined formula (II) are reacted with metallic alkaline earth metals (AE) and optionally the halides thereof in the presence of a metal (M) (in elemental form) and/or the corresponding metal halide ($M^{n+}X^-_n$).

It will be appreciated here that the index n in any metal halide ($M^{n+}X^-_n$) used in the process according to the invention is an integer corresponding to the valency of the metal ion of the metal (M). Preferably, n=2, 3 or 4, especially n=2.

Preference is given to performing the process according to the invention in such a way that, for each equivalent (eq.) of the chloroamine of the formula (II), a total of 1 equivalent or more of metallic alkaline earth metals (AE) and metals (M) in elemental form is used. Preference is given to using a total of more than 1 equivalent of metallic alkaline earth metals (AE) and metals (M) in elemental form, i.e. to working in excess in this regard. Further preferably, for each equivalent of the chloroamine of the formula (II), a total of 1.5 equivalents or more, especially 2 equivalents or more, of metallic alkaline earth metals (AE) and metals (M) in elemental form is used.

In another configuration of the process according to the invention for preparation of AE-complexed metal amides of the above-defined formula (I), chloroamines of the above-defined formula (II) are reacted with a metal (M) in elemental form and optionally the corresponding metal halide ($M^{n+}X^-_n$) in the presence of metallic magnesium, metallic calcium, magnesium halides and/or calcium halides, preference being given to using, for each equivalent of the chloroamine of the formula (II), a total of 1 equivalent or more of metal (M) in elemental form, further preference to using 1.5 equivalents or more, particular preference to using 2 equivalents or more.

In a preferred configuration of the process according to the invention for preparation of AE-complexed metal amides of the above-defined formula (I), chloroamines of the above-defined formula (II) are reacted with metallic alkaline earth metal (AE) (i.e. metallic magnesium and/or metallic calcium) in the presence of metal (M) in elemental form, where M is as defined above, optionally in the presence of the magnesium halide and/or calcium halide and optionally of the metal halide ($M^{n+}X^-{}_n$), preference being given to using, for each equivalent of the chloroamine of the formula (II), a total of 0.8 equivalent or more of metallic alkaline earth metal (AE), further preference to using 1.0 equivalent or more.

In a preferred configuration of the process according to the invention for preparation of AE-complexed metal amides of the above-defined formula (I), chloroamines of the above-defined formula (II) are reacted with metallic magnesium and/or metallic calcium in the presence of an excess of the metal halide ($M^{n+}X^-{}_n$), where M and X are each as defined above, optionally in the presence of the magnesium halide and/or calcium halide and optionally of the metal (M).

The present invention further provides the metal amides of the formula (I) obtainable by the process according to the invention

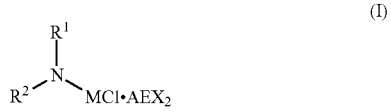

(I)

where the $R^1$, $R^2$ and M, AE and X radicals are each as defined above.

The term "halogen" or "halogen atom" means, for example, fluorine, chlorine, bromine or iodine.

When the term is used for a radical, "halogen" or "halogen atom" means, for example, a fluorine, chlorine, bromine or iodine atom.

Alkyl means a straight-chain, branched or cyclic hydrocarbyl radical. The expression "($C_1$-$C_4$)-alkyl", for example, is a brief notation for alkyl having one to 4 carbon atoms according to the range stated for carbon atoms and encompasses, for example, the methyl, ethyl, 1-propyl, 2-propyl, 1-butyl, 2-butyl, 2-methylpropyl, tert-butyl, cyclopropyl and cyclobutyl radicals.

General alkyl radicals with a larger specified range of carbon atoms, e.g. "($C_1$-$C_6$)-alkyl", correspondingly also encompass straight-chain, branched or cyclic alkyl radicals with a greater number of carbon atoms, i.e. according to the example also the alkyl radicals having 5 and 6 carbon atoms.

Unless stated specifically, for the hydrocarbon radicals such as alkyl radicals, including in composite radicals, preference is given to the lower carbon skeletons, for example having 1 to 6 carbon atoms, or having 2 to 6 carbon atoms in the case of unsaturated groups. Alkyl radicals, including in the composite radicals such as alkoxy, haloalkyl etc., mean, for example, methyl, ethyl, cyclo-, n- or i-propyl, cyclo-, n-, i-, t- or 2-butyl, pentyls, hexyls such as cyclohexyl, n-hexyl, i-hexyl and 1,3-dimethylbutyl, heptyls such as cycloheptyl, n-heptyl, 1-methylhexyl and 1,4-dimethylpentyl.

Preferred cyclic alkyl radicals preferably have 3-8 ring carbon atoms, for example cyclopropyl, cyclobutyl, cyclopentyl or cyclohexyl. In the case of optionally substituted cyclic alkyl radicals, cyclic systems with substituents are included, also including substituents with a double bond on the cyclic alkyl radical, for example an alkylidene group such as methylidene.

In the case of optionally substituted cyclic alkyl radicals, polycyclic aliphatic systems are also included, such as bicyclo[1.1.0]butan-1-yl, bicyclo[1.1.0]butan-2-yl, bicyclo[2.1.0]pentan-1-yl, bicyclo[2.1.0]pentan-2-yl, bicyclo[2.1.0]pentan-5-yl, bicyclo[2.2.1]hept-2-yl(norbornyl), adamantan-1-yl and adamantan-2-yl.

In the case of optionally substituted cyclic alkyl radicals, spirocyclic aliphatic systems are also included, for example spiro[2.2]pent-1-yl, spiro[2.3]hex-1-yl, spiro[2.3]hex-4-yl, 3-spiro[2.3]hex-5-yl.

Aryl is a mono-, bi- or polycyclic aromatic system having preferably 6 to 14, especially 6 to 10, ring carbon atoms, for example phenyl, indanyl, naphthyl, anthryl, phenanthrenyl and the like, preferably phenyl.

When two or more radicals form one or more rings, these may be carbocyclic, heterocyclic, saturated, partly saturated, unsaturated, for example also aromatic and optionally further substituted. The fused rings are preferably 5- or 6-membered rings, particular preference being given to benzofused cycles.

The substituents mentioned by way of example ("first substituent level") may, if they contain hydrocarbonaceous moieties, optionally be further substituted therein ("second substituent level"), for example by one of the substituents as defined for the first substituent level. Corresponding further substituent levels are possible. The term "substituted radical" preferably embraces just one or two substituent levels.

Preferred substituents for the substituent levels are, for example,
halogen, nitro, cyanoalkyl, dialkylamino, alkoxy, aryl, aryloxy, benzyl, benzyloxy, heterocyclyl and trialkylsilyl.

Substituents composed of more than one substituent level are preferably, for example, alkoxyalkyl such as monoalkoxyalkyl or dialkoxyalkyl, alkoxyalkoxy such as monoalkoxyalkoxy or dialkoxyalkoxy, benzyl, phenethyl, benzyloxy, haloalkyl, haloalkoxy, haloalkoxyalkoxy, haloalkoxyalkyl.

In the case of radicals having carbon atoms, preference is given to those having 1 to 6 carbon atoms, preferably 1 to 4 carbon atoms, especially 1 or 2 carbon atoms. Preference is generally given to substituents from the group consisting of halogen, for example fluorine and chlorine, ($C_1$-$C_4$)alkyl, preferably methyl or ethyl, ($C_1$-$C_4$)haloalkyl, preferably trifluoromethyl, ($C_1$-$C_4$)alkoxy, preferably methoxy or ethoxy, ($C_1$-$C_4$)haloalkoxy, nitro and cyano. Particular preference is given here to the substituents methyl, methoxy, fluorine and chlorine.

Substituted amino such as mono- or disubstituted amino is a radical from the group of the substituted amino radicals which are N-substituted, for example, by one or two identical or different radicals from the group of alkyl, alkoxy and aryl; preferably dialkylamino and diarylamino, such as optionally substituted N-alkyl-N-arylamino, and saturated N-heterocycles; preference is given to alkyl radicals having 1 to 4 carbon atoms; aryl is preferably phenyl or substituted phenyl.

Optionally substituted phenyl is preferably phenyl which is unsubstituted or mono- or polysubstituted, preferably up to trisubstituted, by identical or different radicals from the group of halogen, ($C_1$-$C_4$)alkyl, ($C_1$-$C_4$)alkoxy, ($C_1$-$C_4$)alkoxy-($C_1$-$C_4$)alkoxy, ($C_1$-$C_4$)alkoxy-($C_1$-$C_4$)alkyl, ($C_1$-$C_4$)haloalkyl, ($C_1$-$C_4$)haloalkoxy, cyano and nitro, e.g. o-, m- and p-tolyl, dimethylphenyls, 2-, 3- and 4-chlorophenyl, 2-, 3- and 4-fluorophenyl, 2-, 3- and 4-trifluoromethyl- and -trichloromethylphenyl, 2,4-, 3,5-, 2,5- and 2,3-dichlorophenyl, o-, m- and p-methoxyphenyl.

Optionally substituted heterocyclyl is preferably heterocyclyl which is unsubstituted or mono- or polysubstituted, preferably up to trisubstituted, by identical or different radicals from the group of halogen, cyano, $(C_1-C_4)$alkyl, $(C_1-C_4)$alkoxy, $(C_1-C_4)$alkoxy-$(C_1-C_4)$alkoxy, $(C_1-C_4)$alkoxy-$(C_1-C_4)$alkyl, $(C_1-C_4)$haloalkyl, $(C_1-C_4)$haloalkoxy, nitro and oxo, and is especially mono- or polysubstituted by radicals from the group of halogen, $(C_1-C_4)$alkyl, $(C_1-C_4)$alkoxy, $(C_1-C_4)$haloalkyl and oxo, very particularly by one or two $(C_1-C_4)$alkyl radicals.

Haloalkyl is alkyl partly or fully substituted by identical or different halogen atoms, for example monohaloalkyl such as $CH_2CH_2Cl$, $CH_2CH_2F$, $CHClCH_3$, $CHFCH_3$, $CH_2Cl$, $CH_2F$; perhaloalkyl such as $CCl_3$ or $CF_3$ or $CF_2CF_3$; polyhaloalkyl such as $CHF_2$, $CH_2F$, $CH_2CHFCl$, $CHCl_2$, $CF_2CF_2H$, $CH_2CF_3$; haloalkoxy is, for example, $OCF_3$, $OCHF_2$, $OCH_2F$, $OCF_2CF_3$, $OCH_2CF_3$ and $OCH_2CH_2Cl$.

Organic compounds having activated C—H bonds are molecules having an increased tendency to release a hydrogen atom bonded to a carbon atom as protons, and hence, in a formal sense, to act as an acid. This is the case, for example, when the carbon atom is bonded to strongly electron-withdrawing groups such as carbonyls (in an ester, ketone or aldehyde), sulphones, nitriles, trifluoromethyl groups or nitro groups. For example, derivatives of malonic acid (pKa≈13) or acetylacetone (pKa≈9) have activated C—H bonds. C—C multiple bonds, as a result of the proximity of the carbon atoms, likewise ensure stronger polarization, such that α-alkenyl and -alkynyl groups, as, for example, in vinyl and propargyl groups, lead to CH activation. In addition, the formation of aromatic systems can also enhance CH acidity.

According to the present invention, formula (I) also encompasses all tautomers and/or oligomeric or polymeric complexes present in equilibrium, in which coordinating solvents may optionally also be involved in the structures formed. The bond may be formed either via the halides X or via the nitrogen atoms.

The AE-complexed metal amides of the formula (I) obtainable by the process according to the invention are especially suitable for metallation under mild conditions. They are therefore particularly suitable for conversion of sensitive (hetero)aromatics and are tolerated by sensitive functional groups, for example nitro, aldehyde or F, which is frequently not the case for the corresponding lithium or magnesium bases.

TMPZnCl.LiCl has been described in the literature as a mild base for the metallation of sensitive (hetero)aromatics at temperatures around 20° C. (see Org. Lett. 2009, 11(8), 1837-1840). In in-house studies, however, it was found that, for example, the metallation of the sensitive heteroaromatic 4,6-dichloro-5-nitropyrimidine with TMPZnCl.LiCl at 20° C. and the subsequent reaction with an electrophile such as iodine led to the destruction of the 4,6-dichloro-5-nitropyrimidine.

If this reaction of 4,6-dichloro-5-nitropyrimidine, in contrast, is performed under the same conditions with an inventive metal amide of the formula (I), the desired conversion is possible, it being possible to use, as the electrophile ("E"), for example, iodine or else other electrophiles, as shown by way of example hereinafter using the example of the inventive TMPZnCl.MgCl$_2$ and iodine as the electrophile.

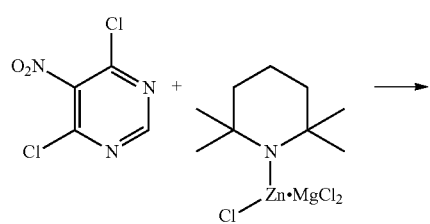

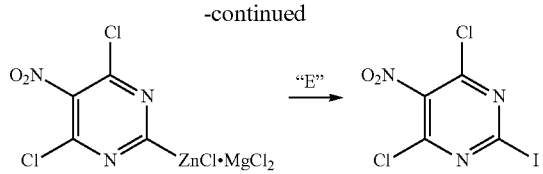

The process according to the invention is to be described in detail by the example, shown in Scheme 1A and 1B below, of the preparation of TMPZnCl.MgCl$_2$ and TMPZnCl.CaCl$_2$, the metallic alkaline earth metal (AE) used in each case being Mg(0) or Ca(0).

Scheme 1A:

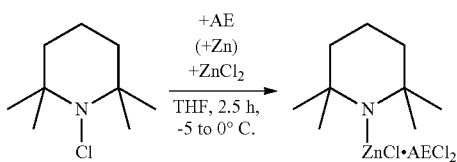

Scheme 1B:

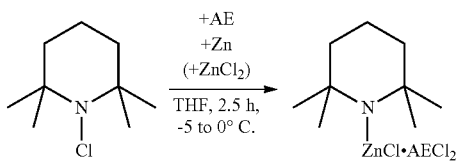

The chloroamines of the formula (II) can be obtained by the methods described in the prior art, for example in Bodor et al. Jour. Pharm. Sci. 1974, 63, 1387; Kovacic et al., Chemical Reviews 1970, 70, 6, 639; Zakrzewski et al, Synthetic Communications 1988, 18 (16&17), 2135; J. Org. Chem. 1997, 62, 16, 5631. Preference is given to effecting the synthesis by reacting the corresponding secondary amines with hypochlorites, as described in JACS, 1973, 6400 or by Toshimasa et al. Bull. Chem. Soc. Jap., 1972, 45, 1802 and Deno et al. JACS 1971, 93, 2065.

A preferred embodiment of the invention relates to the calcium- or magnesium-complexed metal amides of the formula (I), and to a process for preparation thereof, where
AE is calcium or magnesium,
M is a metal selected from Sc, Ti, Mn, Fe, Co, Ni, Cu, Zn and Al;
X is a halogen atom selected from chlorine and bromine;
$R^1$ and $R^2$ together form a —$(CH_2)_4$—, —$(CH_2)_5$— or —$(CH_2)_2O(CH_2)_2$— group in which each of these groups may optionally be substituted by 1, 2, 3 or 4 $R^5$ radicals; therein,
$R^5$ is selected from methyl, ethyl, n-propyl and i-propyl.

A particularly preferred embodiment of the invention relates to the calcium- or magnesium-complexed metal amides of the formula (I), and to a process for preparation thereof, where
AE is calcium or magnesium,
M is a metal selected from Ti, Mn, Fe, Zn and Al;
X is a halogen atom selected from chlorine and bromine;
$R^1$ and $R^2$ together form a —$(CH_2)_5$— group substituted by 4 methyl groups.

Very particular preference is given to using 1-chloro-2,2,6,6-tetramethylpiperidine as the chloroamine of the formula (II) in the process according to the invention.

Thus, the present invention also relates to a AE-complexed metal amide of the formula (I-i)

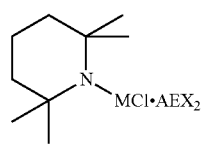

(I-i)

wherein
AE is selected from Ca and Mg;
M is a metal selected from Sc, Ti, Mn, Fe, Co, Ni, Cu, Zn and Al; and
X is a halogen atom selected from chlorine and bromine, preferably chlorine.

Particularly preferred in the context of the present invention are the AE-complexed zinc amides of the formula (I-ii) and the tautomers, oligomers and polymers thereof

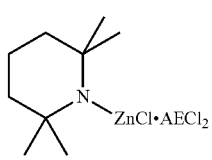

(I-ii)

wherein AE is Ca or Mg.

The process according to the invention is executed preferably within a temperature range from +20 to −20° C., preferably from +10 to −10° C., more preferably from +5 to −5° C.

The reaction is preferably performed under protective gas atmosphere in an aprotic, anhydrous solvent selected from the group consisting of ethers and aromatics, or mixtures thereof. Particular preference is given to using coordinating solvents, for example THF, 2-methyltetrahydrofuran, tert-butyl methyl ether, 1,2-dimethoxyethane or diethyl ether, or else mixtures thereof with aromatics, for example benzene, toluene, ethylbenzene or xylene, and/or else with alkanes or cycloalkanes or alkyl-substituted cycloalkanes, for example n-hexane, n-heptane, cyclohexane, isooctane or methylcyclohexane.

The dilution of the reaction mixture is preferably adjusted such that the resulting solution of the AE-complexed metal amide can be used in subsequent reactions without further concentration.

The reaction mixture can be separated from the metal residues by decantation or filtration.

Based on the chloroamine of the formula (II), the combinations of the alkaline earth metal (AE) and halide thereof (EAX$_2$) and the metal (M) and metal halide thereof (M$^{n+}$X$^-_n$) are preferably used in excess.

According to the present invention, for each equivalent of the chloroamine of the formula (II), up to 5 equivalents each, preferably up to 3 equivalents each, more preferably up to 2 equivalents each, of the alkaline earth metal (AE), of the metal (M), of the alkaline earth metal halide (EAX$_2$) and/or of the metal halide (M$^{n+}$X$^-_n$) are used. To achieve a full conversion of chloroamine of the formula (II), a sum total of at least 1.0 equivalent of the metallic alkaline earth metal (AE) and/or of the metal (M) has to be used. In addition, a total of at least 1.0 equivalent of the metal (M) and/or of the metal halide (M$^{n+}$X$^-_n$) has to be used, it being particularly advantageous to dispense with the alkaline earth metal halide (EAX$_2$).

The combined use of magnesium and calcium and/or halides thereof makes it possible to obtain mixtures of the compounds of the formula (I) which, owing to synergisms, may have advantages, for example elevated solubility.

Metallic magnesium can be used in the reaction in the form of turnings, beads or powder. Owing to the high active surface area, magnesium powder is preferred. Metallic calcium is typically used in the reaction in the form of calcium powder. The calcium source used in the context of the present invention is preferably calcium fluoride, calcium chloride or calcium bromide, more preferably calcium chloride.

Magnesium halides are selected from magnesium fluoride, magnesium chloride, magnesium bromide and magnesium iodide. Preference is given to using magnesium chloride or magnesium bromide, particular preference to using magnesium chloride.

For further activation of the metals, it is optionally possible to use an activating reagent, alone or in combination, for example i-Bu$_2$AlH (DIBAL-H), dibromoethane or iodine.

The metals (M) used in the context of the present invention are selected from metals of groups 3, 4, 7, 8, 9, 10, 11, 12, 13 of the Periodic Table of the Elements (IUPAC nomenclature) or the halides thereof, preferably chlorides, and the group of the lanthanoids or the halides thereof, preferably chlorides; the metals (M) are preferably selected from Sc, Ti, Mn, Fe, Co, Ni, Cu, Zn and Al or the halides thereof, preferably chlorides; the metals (M) are more preferably selected from Ti, Mn, Fe, Zn and Al or the halides thereof, preferably chlorides. In the context of the present invention, zinc (Zn) and zinc chloride (ZnCl$_2$) are of outstanding significance. In addition, in the context of the present invention, manganese (Mn) and manganese halides, preferably MnCl$_2$, are of outstanding significance.

The present invention further provides for the use of the AE-complexed metal amides of the formula (I) obtainable according to a process of the present invention as bases for aromatics, heteroaromatics, alkenes, alkynes and other organic compounds with activated C—H bonds. The basicity, selectivity or activity thereof can be enhanced or advantageously influenced by addition of lithium salts, either in the course of preparation or in the course of use, for example lithium chloride, or by crown ethers or other coordinating reagents.

The present invention is to be illustrated in detail by the examples which follow.

EXAMPLES

Preparation of (TMP)ZnCl.CaCl$_2$ with Ca and Zn

In a dry, argon-filled Schlenk tube with a magnetic stirrer bar and septum, calcium powder (16 mesh—802 mg, 20 mmol) and zinc powder (5231 mg, 80 mmol) were initially charged in anhydrous THF (15 ml) and activated by addition of DIBAL-H (0.1 ml, 1 M in THF). After stirring for 5 min, the mixture was cooled to 0° C. and the stirring was stopped. After the addition of iodine (65 mg, 0.25 mmol), the mixture was stirred again and 1-chloro-2,2,6,6-tetramethylpiperidine (TMPCl; 3.51 g, 20 mmol) in anhydrous THF (15 ml) was added dropwise at −5° C. with an infusion pump (rate: 15 ml/h). Thereafter, the reaction mixture was stirred at 25° C. for 30 min. Subsequently, the metal residues were decanted off and the yellow solution was titrated with benzoic acid and N-phenyl-4-(phenylazo)aniline as an indicator. The concentration was 0.47 M (yield=88%).

Preparation of (TMP)ZnCl.MgCl₂ with Mg and Zn

In a dry, argon-filled Schlenk tube with a magnetic stirrer bar and septum, magnesium powder (325 mesh—1328 mg, 54.7 mmol) and zinc powder (3573 mg, 54.7 mmol) are initially charged and activated by addition of DIBAL-H (0.5 ml, 1 M in THF). After stiffing for 5 min, the mixture is cooled to 0° C. and the stiffing is stopped. After the addition of iodine (65 mg, 0.25 mmol), the mixture is stirred again and 1-chloro-2,2,6,6-tetramethylpiperidine (TMPCl; 2.4 g, 13.7 mmol) in anhydrous THF (15 ml) was added dropwise at 0° C. with an infusion pump (rate: 15 ml/h). Thereafter, the reaction mixture is stirred at 25° C. for another 30 min and the yellow solution is titrated with benzoic acid and N-phenyl-4-(phenylazo)aniline as an indicator. The concentration is 0.38 M (yield=96%).

Preparation of (TMP)ZnCl.MgCl₂ with Mg and ZnCl₂

In a dry, argon-filled Schlenk tube with a magnetic stirrer bar and septum, magnesium powder (325 mesh—1458 mg, 60 mmol) and zinc chloride (42.9 ml, 30 mmol, 0.7 M in THF) are initially charged and activated by addition of DIBAL-H (0.5 ml, 1 M in THF). After stirring for 5 min, the mixture is cooled to 0° C. and the stirring is stopped. After the addition of iodine (65 mg, 0.25 mmol), the mixture is stirred again and 1-chloro-2,2,6,6-tetramethylpiperidine (TMPCl; 3514 mg, 20 mmol) in anhydrous THF (15 ml) was added dropwise at 0° C. with an infusion pump (rate: 15 ml/h). Thereafter, the reaction mixture is stirred at 25° C. for another 8 h and the yellow solution is titrated with benzoic acid and N-phenyl-4-(phenylazo)aniline as an indicator. The concentration is 0.17 M (yield=50%).

The invention claimed is:

1. A process for preparing an AE-complexed metal amide of formula (I)

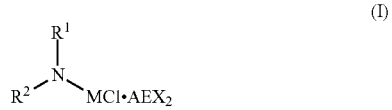

wherein
AE is an alkaline earth metal selected from calcium and magnesium;
M is a metal selected from Sc, Ti, Mn, Fe, Co, Ni, Cu, Zn and Al;
X is a halogen atom selected from the group consisting of fluorine, chlorine, bromine and iodine;
R¹ and R² are each independently selected from the group consisting of (C₁-C₈)alkyl optionally substituted by 1-2 R³ radicals;
or
R¹ and R² together form a —(CH₂)₄—, —(CH₂)₅— or —(CH₂)₂O(CH₂)₂— group, where each of these groups may optionally be substituted by 1-4 R⁴ radicals;
R³ is independently selected from halogen, (C₁-C₃)alkoxy, (C₁-C₃)haloalkoxy and (C₂-C₄)dialkylamino;
R⁴ is selected from halogen, (C₁-C₃)alkyl, (C₁-C₃)alkoxy, (C₁-C₃)haloalkoxy and (C₂-C₄)dialkylamino, by reacting a chloroamine of formula (II)

with one or more alkaline earth metals (AE) in elemental form and one or more metals (M) in elemental form, where R¹, R², AE and M are each as defined above.

2. The process according to claim 1, wherein
AE is an alkaline earth metal selected from calcium and magnesium;
M is a metal selected from Sc, Ti, Mn, Fe, Co, Ni, Cu, Zn and Al;
X is a halogen atom selected from chlorine and bromine;
R¹ and R² together form a —(CH₂)₄—, —(CH₂)₅— or —(CH₂)₂O(CH₂)₂— group, where each of these groups may optionally be substituted by 1-4 R⁵ radicals;
R⁵ is selected from methyl, ethyl, n-propyl and i-propyl.

3. The process according to claim 1, wherein
AE is an alkaline earth metal selected from calcium and magnesium;
M is a metal selected from Ti, Mn, Fe, Zn and Al;
X is chlorine;
R¹ and R² together form a —(CH₂)₅— group substituted by 4 methyl groups.

4. The process according to claim 1, wherein
AE is Ca or Mg;
M is Zn or Mn;
X is chlorine; and
R¹ and R² together form a —C(CH₃)₂(CH₂)₃—C(CH₃)₂— group.

5. The process according to claim 1, wherein
AE is Ca or Mg;
M is Zn;
X is chlorine; and
R¹ and R² together form a —C(CH₃)₂(CH₂)₃—C(CH₃)₂— group.

6. The process according to claim 1, wherein said process is executed within a temperature range from +20 to −20° C.

7. The process according to claim 1, wherein the reacting is performed in a coordinating solvent selected from THF, 2-methyltetrahydrofuran, t-butyl methyl ether, 1,2-dimethoxyethane, diethyl ether, di-n-butyl ether and methyl cyclopentyl ether, or mixtures thereof.

8. The process according to claim 1, wherein the reacting is performed in a mixture of a coordinating solvent selected from THF, 2-methyltetrahydrofuran, t-butyl methyl ether, 1,2-dimethoxyethane, di-n-butyl ether, methyl cyclopentyl ether and diethyl ether, and a noncoordinating solvent selected from aromatics, alkyl-substituted aromatics, alkanes, cycloalkanes and/or alkyl-substituted cycloalkanes.

9. The process according to claim 1 for preparation of an AE-complexed metal amide of the formula (I), wherein the process is performed in the presence of one or more lithium salts.

10. An AE-complexed metal amide of formula (I)

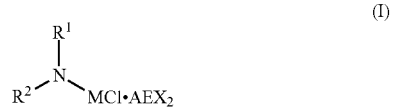

wherein

AE is an alkaline earth metal selected from calcium and magnesium;

M is a metal selected from Sc, Ti, Mn, Fe, Co, Ni, Cu, Zn and Al;

X is a halogen atom selected from the group consisting of fluorine, chlorine, bromine and iodine;

$R^1$ and $R^2$ are each independently selected from the group consisting of $(C_1-C_8)$alkyl optionally substituted by 1-2 $R^3$ radicals;

or $R^1$ and $R^2$ together form a $-(CH_2)_4-$, $-(CH_2)_5-$ or $-(CH_2)_2O(CH_2)_2-$ group, where each of these groups may optionally be substituted by 1-4 $R^4$ radicals;

$R^3$ is independently selected from halogen, $(C_1-C_3)$alkoxy, $(C_1-C_3)$haloalkoxy and $(C_2-C_4)$dialkylamino;

$R^4$ is selected from halogen, $(C_1-C_3)$alkyl, $(C_1-C_3)$alkoxy, $(C_1-C_3)$haloalkoxy and $(C_2-C_4)$dialkylamino, obtainable by the process according to claim 1.

11. An AE-complexed metal amide of formula (I-i)

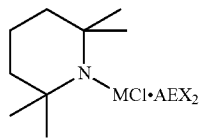

(I-i)

wherein

AE is selected from Ca and Mg;

M is a metal selected from Sc, Ti, Mn, Fe, Co, Ni, Cu, Zn and Al;

X is a halogen atom selected from chlorine and bromine.

12. An AE-complexed zinc amide of formula (I-ii)

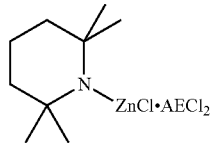

(I-ii)

wherein AE is an alkaline earth metal selected from calcium and magnesium.

13. A method for metallation of one or more aromatics, heteroaromatics, alkenes, alkynes and/or other organic compounds having activated C—H bonds, comprising employing an AE-complexed metal amide according to claim 10 as a base for the metallation.

14. An amide according to claim 10 in the presence of one or more lithium salts.

15. The process according to claim 1, wherein the reacting is performed in a mixture of a coordinating solvent selected from benzene, toluene, xylene, ethylbenzene, cyclohexane, n-heptane, isooctane and/or methylcyclohexane.

* * * * *